United States Patent
Malick et al.

(10) Patent No.: US 6,194,220 B1
(45) Date of Patent: *Feb. 27, 2001

(54) NON-INSTRUMENTED ASSAY WITH QUANTITATIVE AND QUALITATIVE RESULTS

(75) Inventors: Adrien Paul Malick, Granite; Edward Charles McFarland, Parkville, both of MD (US)

(73) Assignee: Becton, Dickinson and Company, Franklin Lakes, NJ (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/719,220

(22) Filed: Sep. 25, 1996

(51) Int. Cl.[7] .................... G01N 33/558; G01N 33/544; G01N 33/543; C12Q 1/00
(52) U.S. Cl. .................... 436/514; 436/535; 436/518; 435/4; 435/7.1
(58) Field of Search .................... 436/514, 539, 436/807, 518; 435/4, 7.1

(56) References Cited

U.S. PATENT DOCUMENTS

| | | | |
|---|---|---|---|
| 3,718,436 | * 2/1973 | Ushakoff | 23/253 |
| 4,435,504 | * 3/1984 | Zuk et al. | 435/7 |
| 4,703,017 | * 10/1987 | Campbell et al. | 436/501 |
| 4,855,240 | * 8/1989 | Rosenstein | 436/514 |

* cited by examiner

*Primary Examiner*—James Housel
*Assistant Examiner*—Brett Nelson
(74) *Attorney, Agent, or Firm*—Bruce S. Weintraub, Esq.

(57) ABSTRACT

The present invention is directed to non-instrumented assays giving quantitative and/or qualitative results. In one embodiment, the present invention is directed to a process and kit determining analyte in a sample wherein the solid support has a contact zone and binder distributed and immobilized throughout the solid support. A sample and a tracer are added to the contact zone and a visible zone is obtained. In another embodiment, the present invention is directed to a process and test wherein the solid support has two contact zones and the binder is not immobilized on the solid support. In this embodiment, the binder is mobile and is added to the second contact zone. At the same time, sample and a tracer are added to the first contact zone. A visible zone is obtained.

9 Claims, 4 Drawing Sheets

NON-INSTRUMENTED ASSAY WITH QUANTITATIVE AND QUALITATIVE RESULTS

FIELD OF THE INVENTION

The invention relates to processes for assaying for an analyte in a sample and to products for utilizing such processes. More particularly, the invention relates to novel solid phase assays.

BACKGROUND OF THE INVENTION

Immunoassay methods, in general, are based on the competition between a specific analyte, the amount of which is to be determined in a sample and a known amount of tracer, which is generally the analyte or appropriate analog thereof in labeled form, with the analyte and tracer competing for a limited number of available binding sites on a binder which is specific for the analyte and tracer.

If the concentration of tracer and binder is fixed and the only variable is the level of analyte, it is possible to establish an assay system for measuring the unknown level of analyte by determining the amount of bound and/or free tracer in the system. The values determined in the assay are compared with the values given by a range of known amounts of the analyte treated in the same manner, and by such comparison, it is possible to determine the amount of analyte in the sample.

In one such procedure, the binder is supported on a solid support, whereby the bound and free components of the assay, after incubation, may be easily separated by separation of the sample and the solid support.

In many cases, the tracers used in such assays require either instrumentation and/or treatment of the tracer in order to determine the tracer in the bound and/or free portion of the assay as a measure of analyte. Thus, for example, in an assay in which an enzyme is used as the label or marker for the tracer, the enzyme must be developed with a suitable developer. When a label or marker is a fluorescent material, the tracer in the bound and/or free portion is determined by the use of appropriate instrumentation for determining fluorescence.

An early test strip device is described by Deutsch, et al., in U.S. Pat. No. 4,361,537. In general, the device comprises a material capable of transporting a solution by capillary action, i.e., a wicking or chromatographic action. Different areas or zones in the test strip contain the assay reagents needed to produce a detectable signal as the analyte is transported to or through such zones. The device is suitable for chemical assays and binding assays and uses a developer solution to transport analyte along the strip.

Many alternatives to or variations on the Deutsch, et al. device have been disclosed. For example, Grubb, et al. (U.S. Pat. No. 4,168,146) describes the use of a porous test strip material to which is covalently bound an antigen-specific antibody. In performing the assay, the test strip is immersed in a solution suspected of containing an antigen, and capillary migration of the solution through the test strip is allowed to occur. As the antigen moves through the test strip it binds to the immobilized antigen-specific antibody. The presence of antigen is then determined by wetting the test strip with a second antigen-specific antibody to which a fluorescent or enzyme label is covalently bound. Quantitative testing can be achieved by measuring the length of the strip that contains bound and labeled antigen.

Tom, et al. (U.S. Pat. No. 4,366,241) describe a device comprised of a test zone (immunosorbing zone) and a liquid absorbing zone in liquid receiving relationship with the test zone. The immunosorbing or test zone has a member of an immunological pair (a "MIP") affixed to a solid support, where the MIP is inhibited from diffusing from the zone. In use, the analyte in the sample solution passes through the immunosorbing zone and binds to the MIP and is concentrated in the immunosorbing zone. The device includes a signal producing system for production of a detectable signal in the test zone in relation to the amount of analyte present in a sample. Tom, et al. teaches the use of the signal producing signal that provides for a detectable signal in the immunosorbing zone which can be compared to a signal level based on a standard having an unknown amount of analyte.

Weng, et al. (U.S. Pat. No. 4,740,468) describe another device and method for performing a specific binding assay. The assay involves both an immobile second binding member which binds to a mobile first binding member and an immobilized analog of the analyte which removes the unbound first binding member from the assay system prior to it being contacted to the detection site.

Greenquist, et al. (U.S. Pat. No. 4,806,311) describe a similar device wherein a first immobilized reagent, such as an analyte-analog is present in a reagent zone to remove free monovalent labeled-binding members from the assay system prior to the test samples contacting the detection layer reagents.

Ullman, et al. (EP 0 271 204 A2) describe a method of determining the presence of an analyte in a sample which is suspected of containing the analyte consisting of contacting a piece of bibulous material with a test solution containing the sample and a first specific binding pair member analogous to the analog. The material contains a second specific binding pair member capable of binding analyte to the first specific binding pair member. The second specific binding pair member is non-diffusively bound to the bibulous material at least at a portion thereof between the contact portion and a small situs on the piece separated from the contact portion. The surface area of the situs is substantially less than the material. The situs is capable of binding the first specific binding pair member not bound to the second specific binding pair member. The test solution is allowed to traverse the material by means of capillary migration and contact the situs. The situs is then examined for the presence of a specific binding pair member which is usually indicated by the presence of a detectable signal. The patent discloses that the signal can be directly detectable or the situs can be exposed to a signal producing means capable of interacting with the first specific binding pair member to produce a detectable signal at the situs in relation to the amount of analyte in the sample. May, et al. (E.P. 0 291 194 A1) disclose an analytical test device comprised of a hollow casing containing a dry porous carrier which communicates with the exterior of the casing such that a sample can be applied to the carrier. The device also contains a labeled specific binding reagent for an analyte which is freely mobile within the carrier. The device further contains an unlabeled specific binding reagent for the same analyte which is permanently immobilized in a detection zone on the carrier. The labeled reagent and detection zone are positioned such that when a liquid sample is applied to the device it can pick up the labeled reagent and thereafter permeate into the detection zone. The device also incorporates a means for indicating the extent, if any, to which the labeled reagent becomes bound in the detection zone. The binding of the labeled reagent can be observed by the user. The patent discloses that a plurality of detection zones arranged in a series on the porous solid phase material, through which the aqueous liquid sample can pass progressively, can also be used to provide a quantitative measurement of the analyte.

Ching, et al. (EP 299 428 A2) describe assay methods and devices utilizing colloidal particle labeled binding materials which are chromatographically mobile and capable of producing visual detectable signals. The method includes contacting the sample with a chromatographic medium having at least one reaction site which includes an immobilized reagent capable of binding a colloidal particle labeled material (which is capable of producing a detectable response) and the substance in the sample. The colloidal particle labeled material is transported on the chromatographic medium such that a portion of the material is transported to the reaction site and is bound thereto. The method that is taught in the patent is concluded by determining the detectable response produced by the colloidal material at the reaction site which indicates the presence or amount of the substance in the sample. An embodiment (competition-type) is described wherein the quantity of analyte present in the sample determines the amount of labeled first reagent which binds at the first zone. The patent teaches that adjustments to the quantity and/or binding affinity of the labeled first reagent can be made in order to determine the quantity of analyte present in the sample.

Sargeant, et al. (EP 0 296 724 A2) disclose an apparatus for determining the presence and/or amount of an analyte in a liquid sample. The patent discloses an apparatus comprised of a non-bibulous lateral flow membrane which is used as an assay substrate. The membrane has an application zone adapted to receive the sample. The membrane also includes an indicator zone spaced laterally from the application zone. The affixed end of the indicator zone is a member of a binding pair capable of binding the analyte or a derivative of the analyte. The patent teaches that the lateral spacing of the application zone and the indicator zone is configured such that liquid introduced at the application zone is caused to flow by non-bibulous flow through the indicator zone. Consequently, utilizing the device as disclosed in the patent, a sample is applied to the substrate and allowed to flow laterally through the indicator zone. Any analyte in the sample is complexed by the affixed specific binding member and detected. The patent discloses that by varying the amount of specific binding pair member in a multiplicity of indicator zones on the membrane, the assay can be made semiquantitative. Consequently, they teach that by calibrating serial dilutions of a binding pair member preparation, affixed over a series of indicator zones, to varying concentrations of analyte, at least a semiquantitative result can be obtained.

Gordon, et al. (EP 0 262 328 A2) disclose test strips for analysis of analytes such as antigens, antibodies, and polynucleotides in a sample by means of a sequential series of reactions. A strip is comprised of a length of chromatographic material having a first end, at which chromatographic solvent transport begins, and a second end, at which chromatographic solvent transport ends, and a plurality of zones positioned between the first and second ends. The first zone is impregnated with the reagent which is mobile in the solvent and capable of reaction with and immobilization against solvent transport by the analyte when the analyte is in an immobilized form. The second zone receives the sample. A third zone is impregnated with another reagent which is immobilized against solvent transport. The reagent is capable of selective reaction with the analyte so as to render the analyte in an immobilized form in the third zone. The patent generally discloses detection means wherein the presence of an analyte in a sample renders a positive color reaction and wherein the absence of analyte renders no color reaction.

Olson, et al. (EP 0 259 157 A1) describe a method for determining the presence of an analyte in a sample which includes utilizing a piece of bibulous material capable of being traversed in at least one direction by a test solution through capillary migration. The test solution is comprised of a sample, an antibody for the analyte, a conjugant of the analyte, and a label. The bibulous material contains a first receptor for the conjugant non-diffusively bound to a situs on the bibulous material separated from a contact portion. The contact portion of the bibulous material provides for contacting with the test solution. The bibulous material further contains a second receptor capable of binding the antibody for the analyte. The second receptor is non-diffusively bound to the bibulous material at least between the situs and the contact portion. The patent discloses that in practicing the method of the alleged invention, the contact portion of the bibulous material separated from the situs is contacted with the test solution which traverses the bibulous material by means of capillary action. After the test solution is allowed to traverse the bibulous material, the situs is examined for the presence of conjugate. The patent discloses that the situs can be exposed to a signal-producing means capable of interacting with the label to produce a signal in relation to the amount of analyte in the test solution.

Olson, et al. further disclose an embodiment wherein the first receptor is conjugated to particles which are non-diffusely bound to the bibulous material at the situs. The patent teaches that the situs can be a narrow or wide band running transverse to the direction of traversal of the test solution along the material. It is stated that a signal produced at the situs can be a narrow or wide band, a sharp-edged distinctive pattern, or the like. The signal generated at the situs can be compared with adjacent areas on the bibulous material. The patent teaches that in some quantitative assays, the signal can be measured directly at the situs without comparison to adjacent areas on the bibulous material.

Deutsch, et al. (EP 0 189 925 A2) describe a process for determining the presence of a particular immunological component in a test sample, comprising immobilizing at one end of a wick a specimen of said immunological component or of an immunological component specific to it. Passing the sample through the wick with a first reagent comprised of an enzyme conjugated to another immunological component which is either specific to the immunological test component or an immunologically comparable to the test sample, whereby the enzyme-carrying reagent attaches to antigen sites if such sites have not previously been filled by the immunological component in the test sample. The process disclosed includes then passing through the wick by capillary action a second reagent containing a substrate acted upon by the enzyme of the first reagent and determining the extent of enzymatic reaction which indicates the amount of immunological component in the initial sample. The extent of enzymatic reaction may be observed by a color change. Deutsch, et al. generally state that the color change or fluorescence may be qualitative, that is, yes or no as in a pregnancy test, or it can be quantitative.

Litman, et al. (EP 0 160 467 A2) describe a protocol which incorporates an enzyme substrate on a bibulous support to which is conjugated a member of a specific binding pair. Upon introduction of the support into the assay medium, the support diffuses into the medium, eliminating a separate development step for the assay. The patent discloses that the result of the assay is determined by a change in the development of color as a result of enzyme catalyzed product formation from the substrate.

Litman, et al. describe two devices: an immunochromatograph and a dip-stick. The dip-stick embodiment is stated to involve one or two elements, where one element is the sample element and the other element is the standard. The immunochromatograph involves a bibulous support providing liquid travel through capillarity, a non-diffusively bound MIP, and also includes one or more members of the signal producing system, i.e., at least one substrate. The immunochromatograph involves a bibulous support which provides a stationary solid phase and an assay medium which provides a moving liquid phase. The region in which the MIP is uniformly non-diffusively bound to the bibulous support is referred to as the immunosorbing zone. The analyte from the sample traverses the zone being carried along with a solvent whose front traverses the zone. The analyte, which is the homologous or reciprocal MIP to the MIP bound to the support, becomes bound to the support through the intermediacy of MIP complex formation. The signal producing system provides the manner in which the area in the immunosorbing zone to which the analyte is bound may be distinguished from the area in which it is absent, so that the distance from a predetermined point on the immunochromatograph is a measure of the amount of analyte in the sample.

Weng, et al. (U.S. Pat. No. 4,879,215) describe a method for determining the presence of an analyte in a sample suspected of containing the analyte wherein the analyte is a member of a specific binding pair consisting of a ligand and its complimentary receptor. The method includes contacting a bibulous material with a test solution containing the sample and a first specific binding pair member capable of binding to the analyte. The material contains a second specific binding pair member non-diffusively bound to a small situs on the material separated from the contact portion. The second specific binding pair member binds the first specific binding pair member when the first specific binding pair ("sbp") member is bound to the analyte. In addition, when the second sbp member is able to bind the first sbp member which is not bound to the analyte, an analyte analog capable of binding the first sbp member is non-diffusively bound to the material. The test solution is allowed to traverse the material by means of capillary migration and the presence of the first specific binding pair member is detected at the situs. The method includes a signal producing system which comprises a labeled-sbp member conjugate and other reagents required to produce a signal at the situs in relation to the presence or amount of analyte in the sample.

Bahar, et al. (U.S. Pat. No. 4,868,108) describe an assay employing two antibodies wherein a microporous carrier supports a plurality of layers, in which conjugates form between test antigens and antibodies. Quantitative results are said to be obtained from an immobilized antibody within an indicating substrate. An apparatus is described for indicating the test antigen in the solution comprised of the following: a porous support having a plurality of regions, a first antibody bound to an enzyme to form an enzyme-linked antibody disposed within one of the regions, a second antibody immobilized within a region different from the first antibody, and a substrate disposed in a region other than the regions of the antibodies which is capable of reacting with the enzyme to yield an indication of test antigen. In addition, the patent teaches that the regions are disposed such that solution flows through the region of the first antibody to the region of the second body and then to the region of the substrate.

Friesen, et al. (U.S. Pat. No. 4,861,711) describe a solid diagnostic device for the quantitative determination of substances of biological affinity in biological fluids. They describe a device comprised of a layer of a plurality of planar zones adjacent one another and in absorbent contact with one another. The layer includes application, intermediate, and absorption zones. The zones are positioned such that the liquid is capable of moving by absorption from the application zone through the intermediate zone onto the absorption zone. The intermediate zone comprises a solid phase zone having at least one unlabeled reactant capable of interactions of biological affinity with at least one analyte. Disposed in an area between the application zone and the solid phase zone is at least one unattached, labeled reactant or conjugant, capable of interactions of biological affinity with at least one analyte. In addition, the device includes an analyte application zone disposed at the mobile phase application zone or in between the mobile application zone and the absorption zone. The analyte application zone is disposed such that after application of an analyte, the analyte is reacted with the reactants in the layer and is detected in the layer.

Ullman, et al. (U.S. Pat. No. 4,857,453) describe a device for conducting an assay method. The device comprises a housing. Enclosed within the housing is a means for capturing a member of a specific binding pair in a zone and for allowing liquid to be transported by capillary action away from the zone. Also enclosed in the housing are one or more self-contained reagents for conducting an assay method for determining an analyte in a sample. In addition, the housing includes means for introducing a sample to the device. The patent teaches that preferably liquid reagents are combined in at least one breakable container enclosed in the housing. In relation to a quantitative readout, the patent teaches that the device may possess on its face a scale to assist in quantitating the amount of analyte in the sample.

Rosenstein, et al. (U.S. Pat. No. 4,855,240) describe a test device and assay for determining analyte. The device is constructed such that a tracer and a sample may be simultaneously applied to different absorbent material portions both in capillary flow communication with another absorbent material portion having a binder supported thereon. The device is constructed such that the sample contacts the binder prior to any substantial contact between sample and/or tracer and binder. Specifically, the patent discloses an assay employing an absorbent solid support having first, second, and third portions. The first portion receives a sample to be assayed. The second portion receives a tracer and said third portion includes a binder for the analyte. The third portion is in capillary flow communication with the first and third portions. The process includes moving tracer and sample by capillary flow across the binder and the third portion to provide contact between sample and binder prior to substantial contact of the tracer with either the binder or sample. The analyte is determined by determining at least one of the tracers bound in said third portion or tracer which passes across that third portion. The patent further discloses that the preferred tracer is comprised of a ligand and a particulate label, and the particulate label preferably provides a tracer which is visual under the assay conditions so that the presence and/or amount of analyte may be determined without further treatment and without the use of instrumentation, e.g., by use of a liposome containing a dye as the particulate label.

Wie, et al. (GB 2 180 645 A) describe a device to determine the presence of a minute amount of a specific substance in a liquid medium in the form of a test card which includes top and bottom sheets adhesively secured to an intermediate frame member which, together with the top and bottom sheets, defines a filter chamber housing a flat filter. The test portion of the filter includes a binding substrate to which antibodies of the specific substance have been bound. The patent further discloses that a control area on the filter body may be provided which is juxtaposed to the test area. The control area incorporates the same binding substrate and antibody as the test area and is located in the proximity to a control port. The control port is subjected to certain method steps of the invention to provide a control reading which can be compared with the test reading resulting from the administration of the test sample to the test port.

Perry, et al. (PCT/GB88/00329; WO 88/08536) describes an enzyme-labeled binding assay device comprised of an absorbent material and a developing solution containing a substrate for the enzyme. The material is provided with a plurality of reagent zones including an indicator reagent zone. The indicator reagent is capable of immobilizing an enzyme-labeled reagent in an amount dependent on the assay result. The absorbent material includes a reagent that prevents signal formation except where enzyme-labeled reagent is immobilized at the indicator reagent zone. The enzyme and substrate are chosen such that when in contact they produce a signal, such as color formation which may be readily determined. In addition, according to one embodiment described, the intensity of the signal at the indicator zone is inversely proportional to the concentration of the analyte in the sample. The device can be employed to provide quantitative assay results wherein the intensity of the signal produced at the indicator zone will be either proportional to or inversely proportional to the concentration of analyte present in the sample. Consequently, the indicator zone following an assay may be inserted into a reflectance spectrophotometer or a fluorometer, to measure the intensity of the signal produced.

Baker, et al. (PCT/GB 86/0067; WO 87/02774) describe a device for performing an enzyme-labeled binding assay comprised of an absorbent material and a developing solution. The absorbent material is provided with a plurality of reagent zones. One of the zones is an indicator reagent zone and is capable of transporting the developing solution sequentially through each reagent zone. The indicator reagent zone includes a reagent capable of immobilizing an enzyme-labeled reagent in an amount dependent upon the assay result. The developing solution includes a signal-producing substrate for the enzyme.

The results of an assay utilizing the disclosed device may be qualitative, read simply by the absence or presence of a signal, especially a colored signal at the indicator reagent zone. In addition, the device can be employed to provide quantitative assay results. The intensity of the signal-produced at the indicator reagent zone can be either proportional to or inversely proportional to the concentration of an analyte present in the sample. As a result, the indicator reagent zone of the device may, following an assay, may be inserted into a reflectance spectrophotometer, or a fluorometer to measure the intensity of the signal produced. In addition, the indicator reagent zone may be elongated in the direction of developing solution migration or a plurality of individual indicator reagent zones may be provided. Thus, the length of signal produced at the indicator reagent zone or the number of individual zones which exhibit this signal will be quantitative and proportional to, or inversely proportional to, the concentration of analyte in the sample.

Campbell, et al. (U.S. Pat. No. 4,703,017) describe a solid phase assay for an analyte wherein binder is supported on a solid support, such as nitrocellulose, and a tracer is comprised of a ligand labeled with a colored particulate label, such as a liposome including a dye. The assay described in this patent has a high sensitivity, and the tracer is visible on the support under assay conditions, whereby tracer can be determined without instrumentation, and without further treatment thereof.

Figure 1:
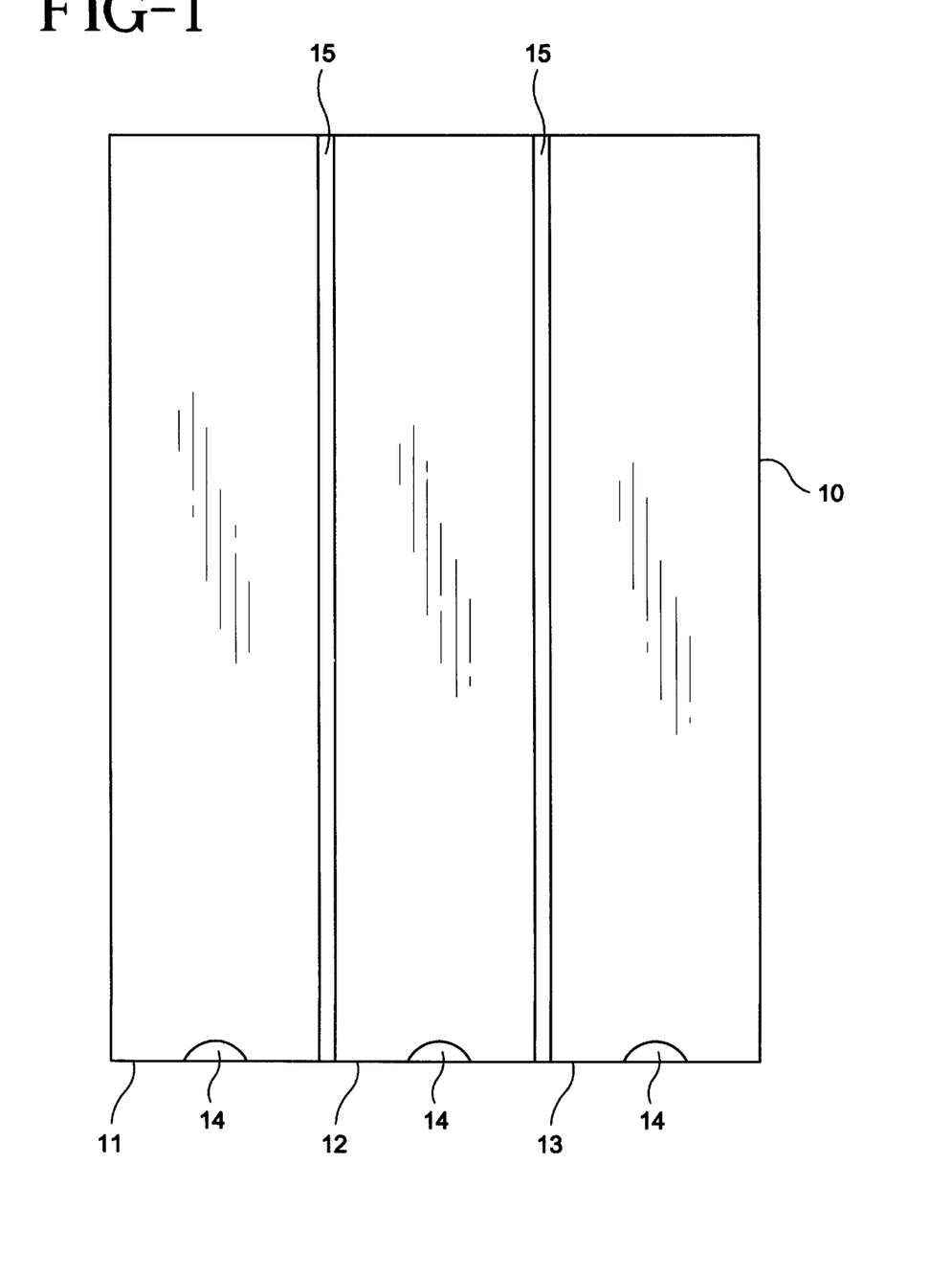
FIG. 1 is a schematic vertical view of a first embodiment of a device of the present invention.

In FIG. 1, the Campbell, et al. patent discloses a test substrate, in the form of a sheet, which is formed preferably from nitrocellulose. The sheet includes three specified distinct test areas each of which is provided with binder. The binder may be an antibody, and the analyte can be a hapten or antigen. The antibody is applied to the three test areas. The remainder of the test strip or sheet includes a suitable blocking agent to prevent non-specific binding. The patent discloses that the three test areas may be provided with antibodies to the analyte having a different affinity for the analyte, with one test area having a high affinity for the analyte, another test area having a moderate affinity for the analyte, and the third test area having a low affinity for the analyte. Alternatively, the test areas may be provided with antibody having the same affinity for the analyte, with the first test area having a high concentration of antibody, the second test area having a medium concentration of antibody, and the third test area having a low concentration of antibody.

Rosenstein (EP 0 284 232 B1) describes an assay device comprising a test strip having a first portion and a second portion. The first and second portions are in the same plane such that material can flow by capillary action from one portion to the other. The first portion includes a tracer comprised of a ligand (specific for the analyte when the device is configured for a sandwich assay and is the analyte or analog thereof when the device is configured for a competitive assay) conjugated to a non-soluble particulate marker. The first portion is also the situs for the addition of the sample to the device. The second portion has a binder immobilized in it (which is specific for the analyte when the device is configured for a sandwich assay and is specific for the analyte and ligand when the device is configured for a competitive assay). The binder is present in the second portion in an amount sufficient such that the tracer bound in that portion is visible. This patent teaches that in an assay, the determination of a tracer and/or analyte may be either qualitative or quantitative.

Donovan, et al. (PCT/US93/08417; WO 94/07141) describe assay devices and methods utilizing dual pathways which provide for the confirmation of assay results. According to one embodiment disclosed, a sandwich-type assay device is described which includes a solid phase having at least two separate fluid-flow pathways. The first pathway contains an assay capture site and the second pathway contains both a confirmatory reagent and a confirming assay site. The first and second pathways may be two individual pieces of porous material or two separate portions of a single porous material. A specific binding member which binds a labeled analyte complex is immobilized both in the first pathway at the assay capture site and in the second pathway at the confirming assay site. The device further contains a confirmatory reagent involving an unlabeled specific binding member which binds the analyte and inhibits the binding of the analyte or labeled analyte complex in the confirming assay site. After the test sample is contacted to the device, the labeled analyte complex becomes immobilized within the first pathway at the assay capture site to indicate the presence or amount of an analyte in the test sample. In the second pathway, the confirmatory reagent blocks the binding of the analyte or labeled analyte complex to the confirming assay site, thereby confirming that the presence of the label in the assay capture site indicates a positive test sample.

Also disclosed is a competitive assay device which includes a solid phase having at least first and a second separate fluid-flow pathways. The first pathway contains an assay capture site and the second pathway contains both a confirmatory reagent and a confirming assay site. An immobilized specific binding member, which competes with the analyte for binding a labeled reagent, results in the binding of the labeled reagent in inverse proportion to the presence or amount of the analyte in the test sample. The binding member is immobilized both in the first pathway at the assay capture site and in the second pathway at the confirming assay site. The device further contains a confirmatory reagent comprising an unlabeled specific binding member which blocks the binding of the analyte in the confirming assay site. The test sample is contacted to the device, and a confirmed positive result is one in which the device displays a decrease in signal or no signal at the assay capture site whereas the confirming assay site displays a detectable signal. The patent teaches that in a preferred embodiment, a visually detectable label is used as the label component of the labeled reagent, thereby providing for the direct visual or instrumented readout of the presence or amount of analyte in the test sample without the need for additional signal producing components at the detection sites.

Pronovost, et al. (EP 0 613 005 A2) describe test articles which comprise a support matrix, and a labeling complex impregnated within the support matrix, wherein the labeling complex comprises a dyed microorganism having a specific binding substance on its cell surface. The patent teaches the accumulation of visible microorganism label may be assessed either visually or by optical detection devices, such as reflectance analyzers and video image analysis and the like. The accumulation of visible label can be assessed either to determine the presence or absence of a label in the capture zone or the visible intensity of accumulated label may be correlated with the concentration of analyte in the biological sample. The correlation between the visible intensity of accumulated label and analyte concentration may be made by comparison of the visible intensity to a reference standard which may or may not be incorporated into the capture zone. Optical detection devices may be programmed to automatically perform this comparison. Visual comparison is said to also be possible by visual evaluation of the intensity with a color key. Swanson, et al. (U.S. Pat. No. 4,073,484) describe a method and apparatus for the quantitative determination of an analyte in a liquid sample. The method and apparatus employ a liquid-permeable solid medium defining a liquid flow path. The medium includes a number of reagent-containing reaction zones spaced apart along the flow path and in which reaction occurs with the analyte or an analyte derivative to result in the formation of a predetermined product. Detector means are employed to detect analyte, analyte derivatives, reactant or predetermined product in the reaction zones, the number of such zones in which such detection occurs indicates the amount of analyte in the liquid. Thus, there is a need for an assay which permits the easy simultaneous qualitative and quantitative determination, e.g., without specific detection and reaction zones, of an analyte by the use of a single device wherein the determination can be made visually without instrumentation and without further treatment.

SUMMARY OF THE INVENTION

The present invention is directed to processes for assaying for an analyte in a sample. For example, in one embodiment the present invention is directed to a process and kit for detecting analyte in a sample wherein a solid support has binder distributed and immobilized on the entirety of the support; sample and a tracer are applied to a contact zone at the front end of the support; the sample and tracer migrate along the solid support to come in contact with the binder on the support and a visible zone is obtained on the support.

In another embodiment, the present invention is directed to a process and kit wherein there are a first and second zone at, respectively, the front and distal ends of the solid support. The first contact zone is contacted with sample suspected of containing analyte and a tracer, the tracer having attached thereto analyte or analyte analog. The second contact zone is contacted with binder for the analyte, wherein the binder has a tracer attached thereto. The binder moves toward the front end of the support and the sample and tracer moves toward the distal end of the support. A visible zone of tracer will be obtained which comprises complexes of tracer-analyte or analyte analog-binder-tracer.

DETAILED DESCRIPTION OF THE PREFERRED EMBODIMENTS

In accordance with one aspect of the present invention, there is provided a method and product for determining presence and amount of an analyte wherein a binder for the analyte and tracer to be used in the assay is supported on the surface of a solid support in a concentration whereby the tracer used in the assay, when bound to the binder, under assay conditions, is visible in the support, without further treatment. Preferably, the tracer used in the assay is a ligand labeled with a label which is visible when bound to the binder on the support, without further treatment, and wherein the ligand is bound by the binder.

In accordance with another aspect of the present invention, there is provided a method and device for determining analytes which are present in test samples in low concentrations wherein the analyte is detected on the surface of a solid support by use of a tracer which is visible. The solid support has a surface area such that the binder is supported in a concentration such that the tracer used in the assay is visible on the support when the analyte is present in the test sample in low concentration. Preferably, the tracer is a ligand labeled with a particulate label, which is visible when the ligand is bound by the binder. In accordance with the present invention, the visibility of tracer (presence and/or absence of visible tracer and the amount of tracer) is determined as a measure of analyte (presence and/or absence and/or amount of analyte).

The solid support which is employed in the assay is generally a cellulose ester, with nitrocellulose giving exceptionally good results. It should be understood that the term "nitrocellulose" refers to nitric acid esters of cellulose, which may be nitrocellulose alone, or a mixed ester of nitric acid and other acids, in particular, aliphatic carboxylic acids having from one to seven carbon atoms, with acetic acid being preferred. Such solid supports which are formed from cellulose esterified with nitric acid alone or a mixture of nitric acid and another acid such as acetic acid, are often referred to as nitrocellulose paper.

Although nitrocellulose is a preferred material for producing the solid support, it is to be understood that other materials, having a surface area sufficient for supporting a binder in a concentration as set forth above may also be employed for producing such solid supports including but not limited to nylon. In general, the support useful in the practice of the present invention has a surface area such that it is capable of supporting binder in a concentration of at least 1 $\mu g/cm^2$ most generally in a concentration of at least 10 $\mu g/cm^2$ and preferably at least 40 $\mu g/cm^2$.

In accordance with a particular preferred embodiment, the pore size of the solid support is such that the tracer (ligand labeled with the particular label), when bound to the binder remains on the surface of the support. Thus, for example, particularly good results have been obtained with a nitrocellulose support having a pore size of from about 0.2 to 0.45 microns.

It is believed the sensitivity of the assay can be increased by increasing the concentration of binder on the support and, accordingly, supports having high surface areas are particularly preferred in that the binder may be supported on such supports in a high concentration. Of course, the concentration of binder which is actually used is dependent in part on the binding affinity of the binder.

The binder which is supported on the solid support is a binder for both analyte and tracer. Thus, for example, if the assay is a competition type of assay, tracer and analyte compete for a limited number of binding sites on the binder.

The type of binder which is used on the assay is dependent upon the analyte to be assayed, as well as the specific assay procedure. As known in the art, the binder which is supported may be an antibody including monoclonal antibodies, an antigen, a protein specific for the material to be bound or a naturally occurring binder. Thus, for example, in a competitive type of assay for an antigen or hapten, the binder may be an antibody or a naturally occurring substance which is specific for the tracer and the antigen or hapten. If the assay is for an antibody, the binder may be, for example, an antigen or an antibody which is specific for the antibody to be assayed. The selection of a suitable binder for support on the solid substrate is deemed to be within the scope of those skilled in the art from the teachings herein.

The ligand which is labeled for use as a tracer in the assay of the present invention is also dependent upon the analyte to be assayed, as well as the assay procedure. Consequently, for example, if a competitive assay is employed for determining antigen or hapten, the ligand employed in producing the tracer would be either the analyte or appropriate analog thereof. (The term "appropriate analog" means that the analog and the analyte is bound by the binder for the analyte.) The selection of a suitable ligand for producing the tracer is deemed to be within the scope of those skilled in the art from the teachings herein.

As indicated above, in producing the tracer, the ligand may, e.g., be labeled with a particulate label, which is visible. A preferred particulate label is a sac, which includes a dye or other colored substance as a marker, whereby the tracer, when used in the assay, is visible without destruction of the sac to release the colored substance.

The sac which is used to label the ligand for producing a tracer may be any one of a wide variety of sacs, including, but not limited to intact erythrocytes, erythrocyte ghosts, liposomes (single walled, sometimes called vesicles, or multilamellar), polymer microcapsules, for example, those made by coacervation, or intrafacial polymerization, etc.

Erythrocyte ghosts are known in the art and are prepared by suspending erythrocyte cells in a solution of substantially lower osmolarity. The ghosts are "resealed" in an aqueous solution including the marker whereby the ghosts include the marker in the interior thereof. Such procedures are known in the art and the resealing solution of appropriate osmolarity generally includes, in addition to the marker, alkali and alkaline earth metal halides and a coenzyme; for example, adenosine triphosphate. The preparation of ghosts, as sacs, is disclosed, for example, by D'Orazio, et al., *Analytical Chemistry*, Vol. 49, No. 13, pgs. 2083–86 (November 1977) which is hereby incorporated by reference.

Polymer microcapsules are also produced by procedures known in the art except that the solution in which the microcapsules are formed also includes a marker whereby the interior of the polymer microcapsule includes the marker. The preparation of such microcapsules is disclosed, for example, in *Microencapsulation Processes and Applications*, edited by Jan E. Vandegger (Plenum Press 1974) which is hereby incorporated by reference.

As known in the art, liposomes can be prepared from a wide variety of lipids, including phospholipids, glyco-lipids, steroids, relatively long chain alkyl esters, for example, alkyl phosphates, fatty acid esters, for example, lecithin, fatty amines and the like. A mixture of fatty materials may be employed, such as a combination of neutral steroid, a charged amphiphile and a phospholipid. The examples of phospholipids include lecithin, sphingomyelin, dipalmitoyl phosphatidylcholine, and the like. Steroids may include cholesterol, cholestanol, anesterol, and the like. The charged amphiphilic compounds may generally contain from twelve to thirty carbon atoms and may include mono- or dialkyl phosphate esters or an alkylamine, for example, dicetyl phosphate, stearyl amine, hexadecyl amine, dilauryl phosphate, and the like.

The liposome sacs are prepared in an aqueous solution including the marker whereby the sacs include the marker in the interior thereof. The liposome sacs are easily prepared by vigorous agitation in the solution, followed by removal of marker from the exterior of the sac. For the preparation of liposomes, see U.S. Pat. No. 4,342,826 and PCT International Publication No. WO 80/01515 which are both hereby incorporated by reference.

The tracer comprised of ligand and particulate label may also be produced by labeling the ligand with an aqueous dispersion of a hydrophobic dye or pigment, or of polymer nuclei coated with such a dye or pigment. Such labels are described in more detail in U.S. Pat. No. 4,373,932, which is hereby incorporated by reference.

Examples of particulate labels which may be used in the present invention include, but are not limited to, ferritin, phycoerythrins or other phycobili-proteins, precipitated or insoluble metals or alloys, fungal, algal, or bacterial pigments or derivatives such as bacterial chlorophylls, plant materials or derivatives and the like.

The ligand may be labeled with a particulate label so as to produce a tracer for use in the invention by procedures generally known in the art, with the procedure which is used being dependent upon the ligand and the particulate label which is employed. Such techniques include adsorption, covalent coupling, derivatization or activation, and the like. In producing a tracer wherein the ligand is labeled with a sac, the sac may be produced from a component which has been derivatized with a ligand, whereby the sac, when produced, is sensitized with the ligand. In another procedure, the sac including the marker may be initially formed, followed by sensitizing the sac with ligand with procedures known in the art.

Thus, the tracer is comprised of a ligand and a particulate label (solid or solid-like, as opposed to non-solid labels such as radioisotopes, enzymes and various fluorescent materials), and the particulate label provides a tracer which is visible under the assay conditions so that the presence and/or amount of analyte may be determined without further treatment and without the use of instrumentation, e.g., by use of a liposome containing a dye as a particulate label.

The solid substrate employed in the assay is preferably in sheet form, with the substrate in sheet form, generally being in the form of a card, a test strip or dip stick, etc. It is to be understood, however, that other forms are also within the spirit and scope of the invention.

The binder is supported on the solid substrate by applying a solution of the binder to the substrate. The binder is generally applied in a concentration of at least 1 $\mu g/cm^2$, most generally at least 10 $\mu g/cm^2$ and preferably at least 40 $\mu g/cm^2$. Although the binder may be appropriately applied to the substrate for support by adsorption, it may also in some cases be necessary or desirable to provide for covalent coupling of the binder to the substrate.

After application of the binder to the substrate, the residual binding capacity of the substrate is preferably saturated or blocked by treatment of the substrate with one or more types of proteins which do not specifically bind the materials to be employed in the assay. Consequently, for example, the residual binding capacity of the substrate may be blocked so as to prevent non-specific binding by the use of bovine serum albumin. The techniques for preventing non-specific binding are generally known in the art, and such techniques are also generally applicable to preventing non-specific binding in the assay of the present invention.

According to one aspect of the invention, an assay technique is provided for determining a hapten or antigen, wherein an antibody is supported on an appropriate substrate. The substrate is preferably formed from nitrocellulose and is contacted and incubated for an appropriate time with a sample containing or suspected of containing analyte. In a particularly preferred embodiment, the antibody is supported on the substrate in a concentration such that under the assay conditions, the tracer which is bound to the support is visible over at least a portion of the analyte range of interest. Subsequently, the substrate is washed with buffer, and contacted with tracer, which is preferably the analyte or appropriate analog thereof coupled to a particular label, preferably a liposome containing a visible dye. The amount of tracer which becomes bound to the supported antibody is inversely proportional to the amount of analyte in the sample. Unbound tracer is rinsed from the substrate and the presence and/or amount of tracer which remains bound to the substrate may be determined as an indirect measure of the presence and/or amount of analyte present in the sample. Consequently, it is possible to visually determine the presence and amount of tracer on the substrate without lysing of the liposome.

In the practice of the present invention, it should be noted that instead of sequentially adding sample and tracer, the substrate containing the supported binder, such as antibody, may be simultaneously contacted with the analyte and the tracer.

In a preferred embodiment, the present invention utilizes migration of an analyte through a solid support and binding of the analyte to a defined zone within the solid support to effect a qualitative and/or quantitative readout. In accordance with the present invention, assays for analytes can be accomplished by varying the type of binder placed on the substrate.

For example, in one type of assay, using digoxin as a representative analyte, it is possible to use a visible tracer, e.g., digoxigenin coupled to a liposome containing a visible dye, such as rhodamine, to provide a visual assay for digoxin. Depending upon the range of interest to be determined, a solid support such as, for example, a nitrocellulose test card, may include varying amounts or dilutions of antibody to digoxin. Additionally, a quantitative assay can be provided by use of a visible tracer as described above, for example, ligand labeled with liposome containing a dye, and a nitrocellulose support on which a binder is supported on the substrate, and subsequently, the use of separate membrane tracks, flow paths, or portions running parallel with the sample membrane track, flow path or portion within the same device and/or support. For example, a quantitative readout is made by including known quantities of analyte in separate portions or membrane tracks running parallel with the sample portion or membrane track within the same device. These known quantities of analyte may be dried into the membrane tracks. Alternatively, known amounts of tracer may be included in the standard tracks or portions. The portions or membrane tracks and locations of tracer, standard/sample are designed to allow standard/sample to traverse the membrane tracks prior to the tracer.

In a particularly preferred embodiment, this assay requires only the addition of a liquid sample or control reagent to start the test and evaluation by the user as to the appearance and size of the colored or clear zone several minutes later at the end of the test.

The quantitative readout is obtained by comparing the size of the colored or clear zone developed by the sample to those of known standards run in the parallel tracks. The size of the zone (colored or clear) will be proportional to the quantity of analyte present.

A qualitative readout is made by looking for the presence or absence of a colored and/or clear zone (depending on the form of the assay).

It is to be understood that the invention can be configured for competitive, as well as standard non-competitive assays thus providing the potential means for detecting a broad range of analytes, including therapeutic drugs, drugs of abuse, hormones, vitamins, proteins (including antibodies of all classes), peptides, steroids, bacteria, fungi, viruses, parasites, components or products of bacteria, fungi, viruses or parasites, allergens of all types, antigens of all types, products or components of normal or malignant cells, etc. In relation to particular examples, the following analytes may be tested for using the present invention: $T_4$, $T_3$, digoxin, hCG, insulin, theophylline, luteinizing hormone, organisms causing or associated with various disease states, such as streptococcus pyogenes (group A), Herpes Simplex I and II, cytomegalovirus, chlamydiae, etc.

The analyte may be determined in various samples, including but not limited to, for example, body fluids, such as urine, serum, etc. In some cases, it may be possible to detect analyte in whole blood.

The invention will be further described with respect to the following FIG. 1, wherein FIG. 1 is a simplified schematic representation of a preferred device in accordance with the invention. The present invention is, however, not intended in any way to be limited to this preferred embodiment.

Referring now to the drawing, there is shown a test substrate, in the form of sheet 10, which is formed preferably from nitrocellulose. Sheet 10 includes specific lanes or portions 11, 12 and 13, each of which has binder immobilized thereon. For purposes of describing the test, the binder is an antibody, and the analyte can be a hapten or antigen. The antibody is applied to tracks or portions 11, 12 and 13, as described above. Preferably, tracks or portions 11, 12 and 13 are provided with antibody having the same affinity for the analyte. However, for quantitative measurement, tracks or portions 12 and 13 contain dried therein known amounts of antigen for comparison to the sample lane or portion 11. It should be noted that FIG. 1 is merely an example. There can be as many or as few tracks/lanes/portions as are necessary to provide a quantitative and/or qualitative readout.

The sample and tracer are applied to the contact zone 14 in the beginning of each lane or portion 11, 12 and 13. Each lane or portion is separated by an impermeable wall or membrane 15 which prevents contact and thus contamination between the lanes or portions 11, 12 and 13.

The present invention is also directed to another method and assay format for detecting analyte in a sample. In this method, the entirety of a solid support is utilized for determining the presence, absence or amount of analyte in a sample. There are two embodiments of this aspect of the present invention.

The first embodiment is directed to a process for detecting analyte in a sample comprising:
  a) providing a solid support wherein said solid support has a contact zone, and has a binder for the analyte distributed throughout the entire length of a solid support and immobilized thereon and further wherein said binder is a binder for at least said analyte;
  b) applying the sample and a tracer having analyte or analyte analog attached thereto to the contact zone;
  c) allowing the sample and tracer to migrate along the solid support to come in contact with binder immobilized on the solid support;
  d) obtaining a visible zone of tracer bound on the solid support; and
  e) determining the presence, absence or amount of said analyte as a function of the location of said visible zone on the solid support.

This embodiment is also directed to a kit for detecting analyte in a sample comprising a solid support as described above.

Figure 2A:
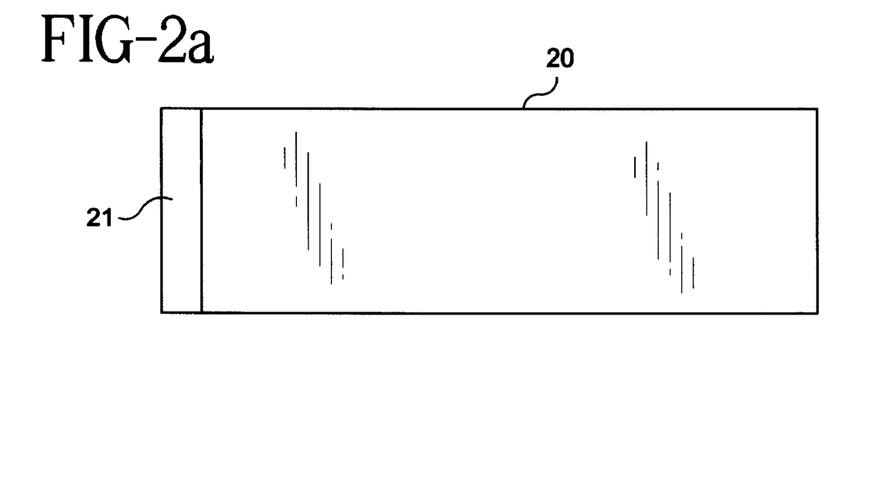
FIGS. 2a–c represent a schematic horizontal view of a second device of the present invention.
Figure 2B:
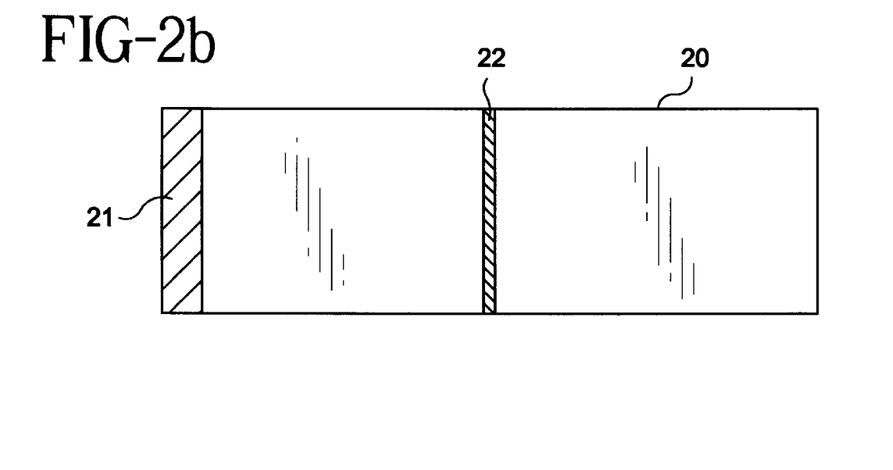

In one example of this embodiment as illustrated in FIG. 2a, the solid support 20 has the binder, which can, for example, be antidigoxin antibody, distributed throughout, and immobilized on, the entirety of the solid support 20. A sample having an analyte which can, for example, be digoxin, is then applied to the contact zone 21 together with a tracer, which can, in this example, be a tracer comprising a liposome containing a dye and surface digoxin attached to the liposome. The sample and tracer can be applied to the contact zone 21 either sequentially or simultaneously. After the sample and tracer migrate by capillary action across the solid support, a visible zone 22 of tracer (a colored band) will appear where the tracer binds to binder. The area between this zone 22 and the contact zone 21 will contain digoxin from the sample which has been bound to binder. A representative example of this result is shown in FIG. 2b. If there is no analyte or minimal analyte in the sample, the visible zone will be much closer to the contact zone. A representative example of this result is shown in FIG. 2c.

It should be further noted that in other embodiments of this aspect of the present invention binder can be distributed throughout less than the entirety of the solid support. For example, binder can be distributed in a specific line or lane running from the front end of the solid support to the distal end of the solid support, and this line or lane of binder can be positioned in the center of the solid support.

Figure 2C:
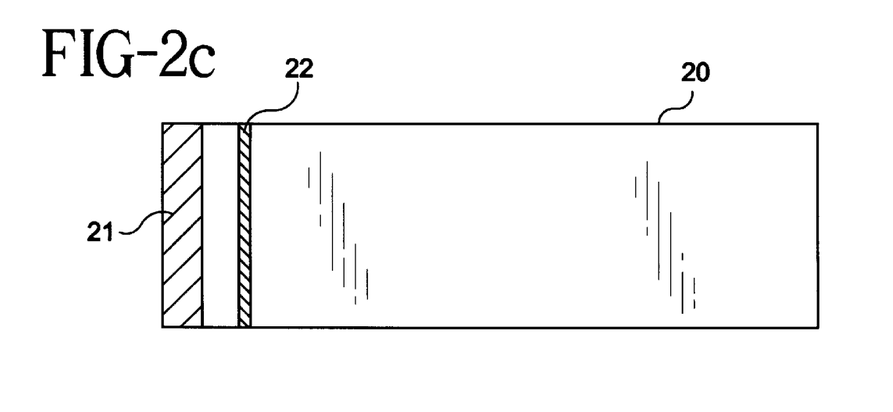

It should be understood that the process and device described above and encompassed in the example shown in FIGS. 2 a–c is a positive read-out system for, for example, small analytes, that make use of their single epitope binding site. Using biotin as a model, if the solid support is coated with anti-biotin, and then exposed to the sample containing biotin, biotin will bind up to a certain point on the solid support. Exposure of the solid support to a tracer which has the analyte on the surface will result in no binding where the analyte bound (all the sites occupied), but then binding will occur at the point on the solid support corresponding to when the analyte was used up. More analyte, then, results in binding of both analyte and (then) detector occurring farther up the solid support resulting in a "positive-readout" system (as contrasted with the typical competitive assay for small analytes, where more analyte results in less signal). See FIGS. 2 a–c.

Another embodiment of the present invention is directed to a process for determining the presence, absence or amount of antibody in the sample, but in this embodiment, binder (for the analyte and tracer) is not distributed and immobilized on the solid support. Instead this process comprises:
  a) providing a solid support having a first and second contact zone, wherein said first contact zone is located at the front end of the solid support and said second contact zone is located at the opposite end of the solid support;
  b) contacting said first contact zone with a sample containing analyte;
  c) contacting said first contact zone with tracer having attached thereto analyte or analyte analog;
  d) contacting said second contact zone with binder for the analyte wherein said binder is attached to a tracer;
  e) obtaining a visible zone of tracer comprising complexes of tracer-analyte or analyte analog-binder-tracer; and
  f) determining the presence, absence or amount of said analyte as a function of the location of said visible zone in the solid support.

This second embodiment also relates to a kit utilizing said solid support.

Figure 3A:
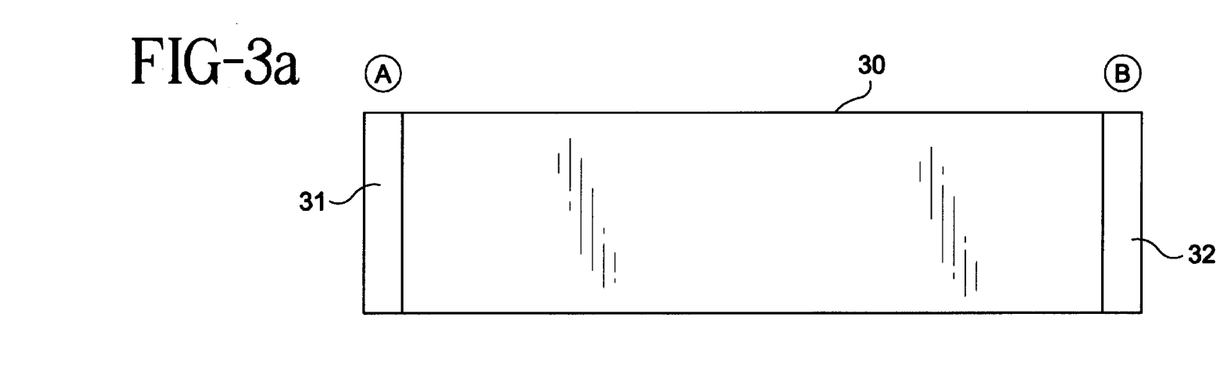
FIGS. 3a–d represent a schematic horizontal view of yet another device of the present invention.
Figure 3B:
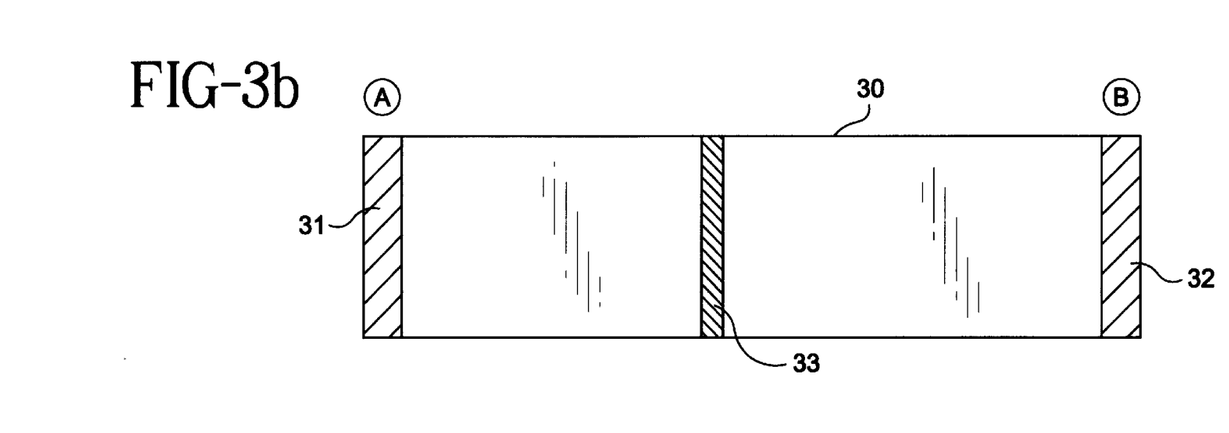
Figure 3C:
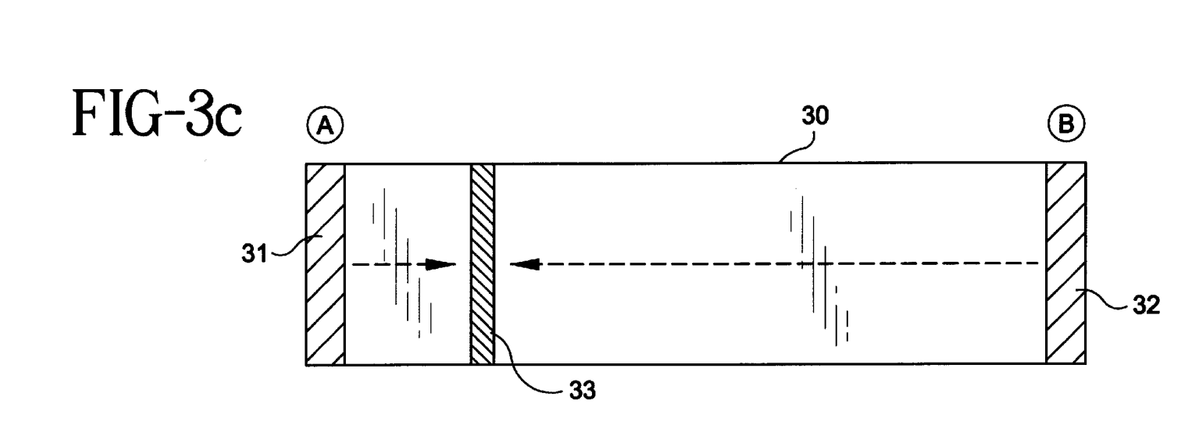
Figure 3D:
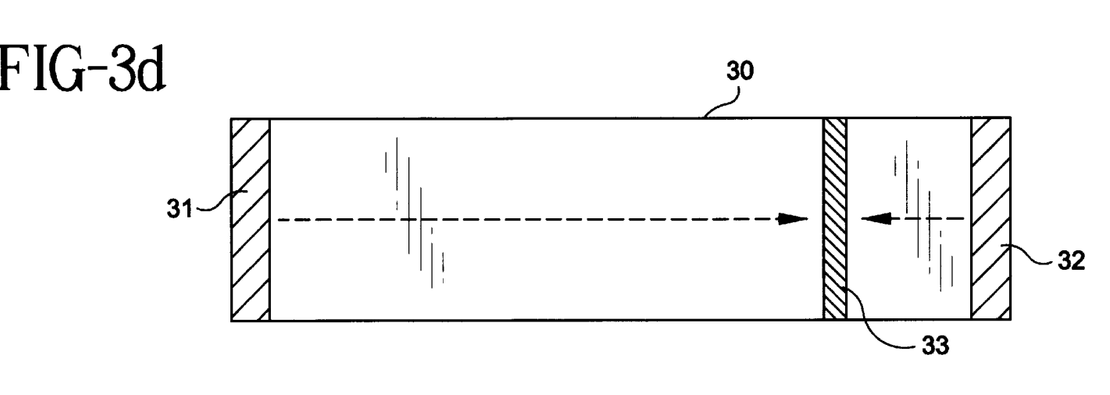

In an example of this second embodiment, as shown in FIG. 3a, this solid support 30 is blocked to prevent any interaction with the reagents. At Point A (the front end) of the solid support, there is a first contact zone 31. A sample containing an analyte which can, for example, be digoxin; and a tracer comprising liposomes having dye contained therein, and digoxin attached thereto, are applied to the first contact zone 31. The tracer and sample are applied to the first contact zone 31. At Point B (the opposite end) of the solid support 30 there is a second contact zone 32. The binder, in this example, is antidigoxin antibodies. The antidigoxin is attached to a tracer, in this case, liposomes having dye contained therein. The antidigoxin-liposomes are applied to the second contact zone 32. The site where the digoxin-liposomes and antidigoxin liposomes meet, bind and form a visible zone or band 33 will represent the concentration of digoxin present in the sample. An example of this result can be seen in FIG. 3b. If there is no digoxin present in the sample then the antidigoxin liposomes will migrate further from the opposite or distal end (Point B) and then form a visible band or zone 33. This result is demonstrated in FIG. 3c. If there is a high concentration of digoxin in the sample then this would block the action on the antidigoxin liposomes and the digoxin liposomes would migrate closer to the distal end (Point B) before forming a visible band or zone 33. This result is demonstrated in FIG. 3d.

It should also be understood that the above two embodiments as described and set forth in FIG. 2 and FIG. 3 are not intended to be limited to the above example. The binder, tracer, analyte to be assayed and solid support of the above described processes (and kits) also set forth in FIG. 2 and FIG. 3 can be any binder, tracer, analyte and solid support as set forth in the present application.

What we claim is:

1. A process for determining the presence, absence or amount of an analyte in a sample in which there is provided a solid support having a first and second contact zone, wherein said first contact zone is located at the front end of the solid support and said second contact zone is located at the distal end of the solid support wherein the process comprises:
    a) contacting said first contact zone with a sample containing analyte;
    b) contacting said first contact zone with tracer wherein said tracer is comprised of analyte labeled with a directly visible label or analyte analog labeled with a directly visible label, without the need for further treatment to said tracer;
    c) contacting said second contact zone with a specific binding member for the analyte wherein said specific binding member is attached to a directly visible label;
    d) obtaining a directly visible zone of tracer comprising complexes of analyte-specific binding member-label or analyte analog-specific binding member-label; and
    e) determining the presence, absence or amount of said analyte as a function of the location of said visible zone in the solid support, without the need for instrumentation to determine said directly visible zone of tracer.

2. The process of claim 1 wherein sample and tracer are sequentially contacted with the first contact zone.

3. The process of claim 1 wherein the sample and tracer are simultaneously contacted with the first contact zone.

4. The process of claim 1 wherein said label is a non-soluble particulate sac including a visible dye.

5. The process of claim 4 wherein the sac is a liposome.

6. The process of claim 1 wherein the solid support is comprised of nitrocellulose.

7. The process of claim 1 wherein the specific binding member is an antibody.

8. The process of claim 1 wherein the analyte is digoxin.

9. The process of claim 1 wherein said label is a non-soluble particulate colored polymeric bead.

* * * * *